US009588206B2

United States Patent
Wu

(10) Patent No.: US 9,588,206 B2
(45) Date of Patent: Mar. 7, 2017

(54) MAGNETIC RESONANCE IMAGING APPARATUS AND HIGH-FREQUENCY MAGNETIC FIELD DERTERMINATION METHOD

(75) Inventor: Binrong Wu, Tokyo (JP)

(73) Assignee: HITACHI, LTD., Tokyo (JP)

( * ) Notice: Subject to any disclaimer, the term of this patent is extended or adjusted under 35 U.S.C. 154(b) by 582 days.

(21) Appl. No.: 14/124,765

(22) PCT Filed: Jun. 27, 2012

(86) PCT No.: PCT/JP2012/066314
§ 371 (c)(1),
(2), (4) Date: Dec. 9, 2013

(87) PCT Pub. No.: WO2013/002231
PCT Pub. Date: Jan. 3, 2013

(65) Prior Publication Data
US 2014/0111204 A1      Apr. 24, 2014

(30) Foreign Application Priority Data

Jun. 30, 2011   (JP) .................................. 2011-146651

(51) Int. Cl.
*G01R 33/54* (2006.01)
*G01R 33/565* (2006.01)
(Continued)

(52) U.S. Cl.
CPC .............. *G01R 33/54* (2013.01); *A61B 5/055* (2013.01); *G01R 33/56518* (2013.01);
(Continued)

(58) Field of Classification Search
CPC .............. G01R 33/54; G01R 33/56518; G01R 33/56572; G01R 33/583; G01R 33/288; A61B 5/055
See application file for complete search history.

(56) References Cited

U.S. PATENT DOCUMENTS 8,582,845 B2 * 11/2013 Ootsuka ........... G01R 33/56572
382/128
2011/0245655 A1 * 10/2011 Abe ................... G01R 33/4816
600/410
(Continued)

FOREIGN PATENT DOCUMENTS

JP          7-171125         7/1995
JP          8-191822         7/1996
WO     WO2011-148783    12/2011

OTHER PUBLICATIONS

International Search Report in PCT/JP2012/066314, Jul. 31, 2012.
(Continued)

*Primary Examiner* — Rodney Bonnette
(74) *Attorney, Agent, or Firm* — Cooper & Dunham LLP

(57) ABSTRACT

According to this invention, in order to obtain high-quality images even when the slice selective gradient magnetic fields waveform is distorted by eddy currents and vibration, high-frequency magnetic field information is calculated on the basis of an output gradient magnetic field waveform applied in accordance with the input gradient magnetic field waveform that is set in a pulse sequence, and the calculated high-frequency magnetic field information is set in the pulse sequence. Then, the set input gradient magnetic field, and the excitation RF pulses of the calculated high-frequency magnetic field information are used during imaging. The output gradient magnetic field waveform used in determining the excitation RF pulses is found by measurement and calculation, for example, by using the input gradient magnetic field waveform.

12 Claims, 11 Drawing Sheets

(51) Int. Cl.
    *G01R 33/58*     (2006.01)
    *G01R 33/28*     (2006.01)
    *A61B 5/055*     (2006.01)

(52) U.S. Cl.
    CPC ..... *G01R 33/56572* (2013.01); *G01R 33/583* (2013.01); *G01R 33/288* (2013.01)

(56) References Cited

U.S. PATENT DOCUMENTS

2013/0069650 A1    3/2013  Abe
2014/0125333 A1*   5/2014  Hanada ............ G01R 33/56518
                                                      324/307

OTHER PUBLICATIONS

C. Schroeder et al., "Slice Excitation for Ultrashort TE Imaging", Proc. Intl. Soc. Mag. Reson. Med. May 12, 2004, #628.
Xiaohong Joe Zhou et al., "A method to Compensate Eddy Current Perturbation for Spatial-Spectral Pulses", Proc. Intl. Soc. Mag. Reson. Med. May 6, 1998, #2057.
Yuval Zui, "Calibration Pre-Scan for Spectral Spatial Pulses", Proc. Intl. Soc. Mag. Reson. Med. May 7, 1999, #2078.
P.E. Larson et al., "Constant Time VERSE for RF Amplitude Reduction in Spectral-Spatial Pulses with Improved Timing Robustness", Proc. Intl. Soc. Mag. Reson. Med. May 16, 2008, #3140.
Peter Latta et al., "Simple phase method for measurement of magnetic field gradient Waveforms", Magnetic Resonance Imaging Feb. 25, 2007, 1272.

* cited by examiner

FIG. 4
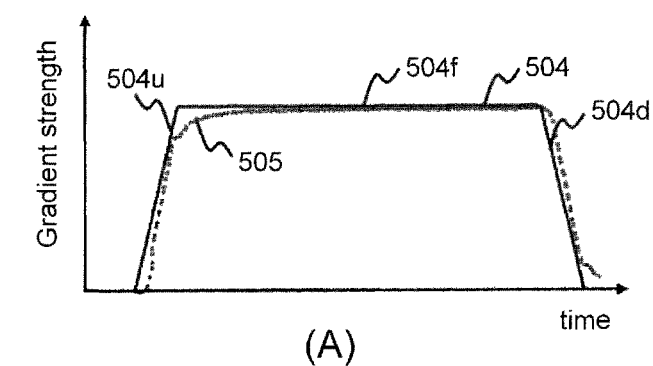
(A)
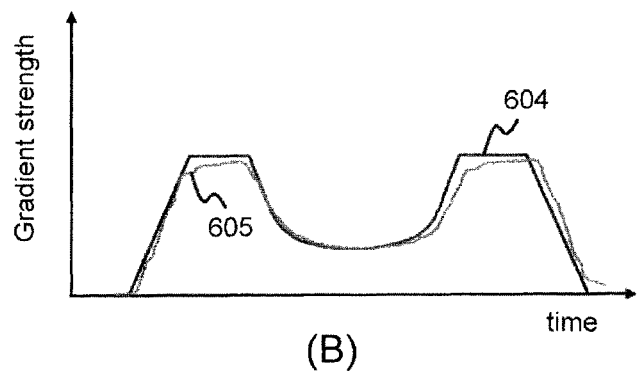
(B)

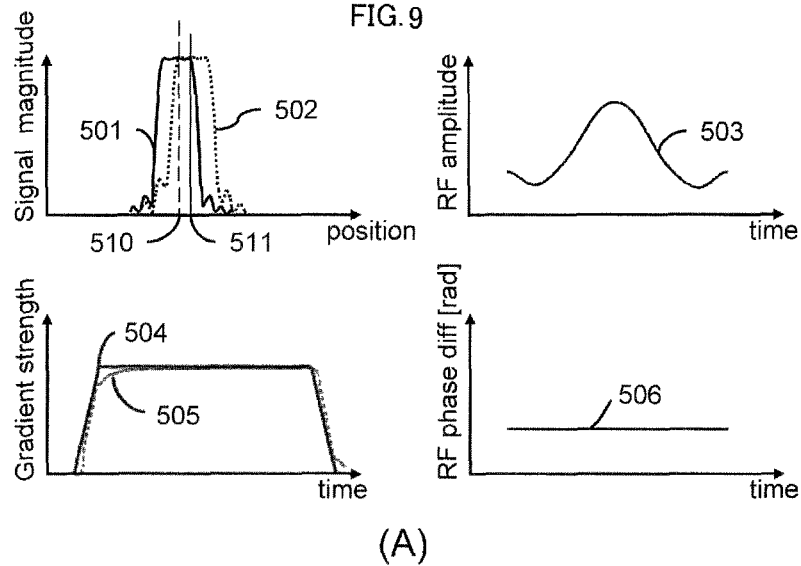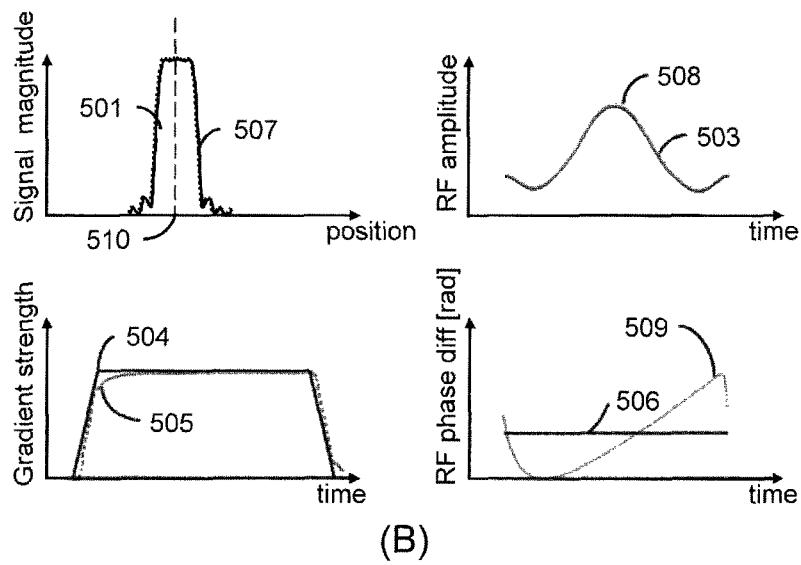
FIG. 9

FIG.10
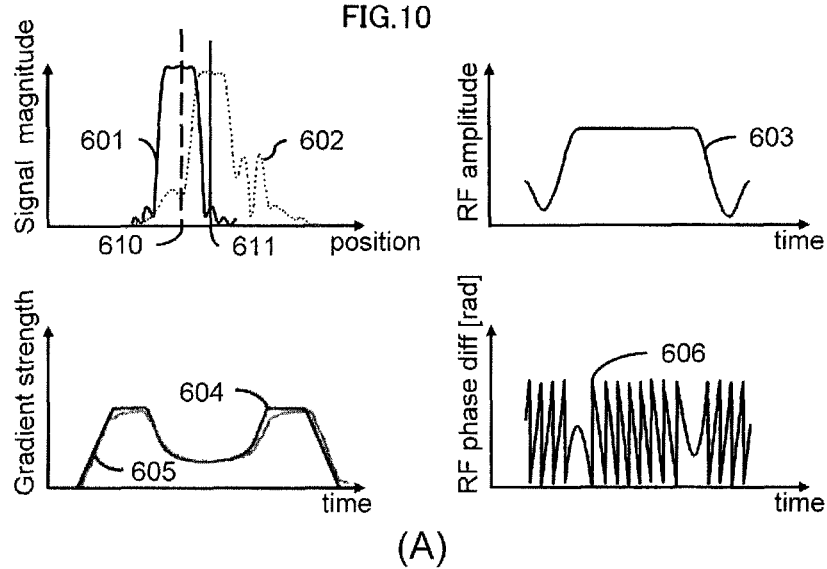
(A)
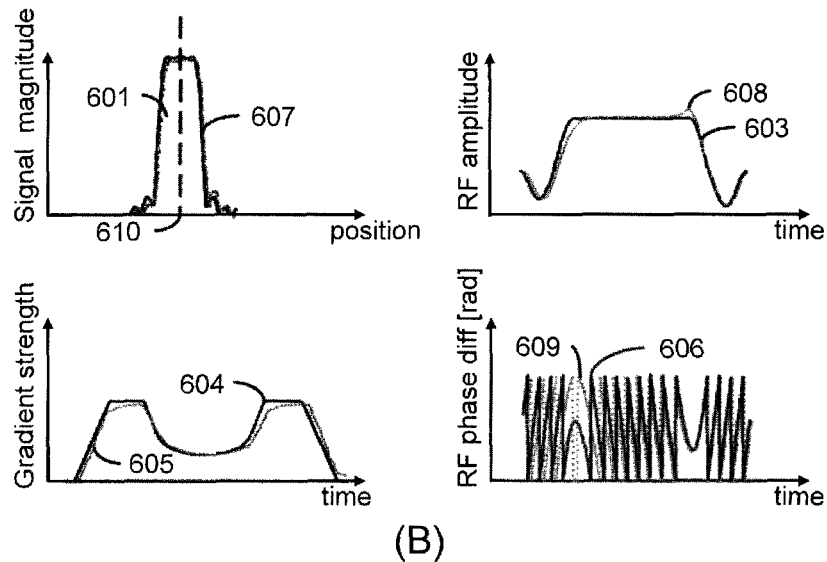
(B)

FIG. 11
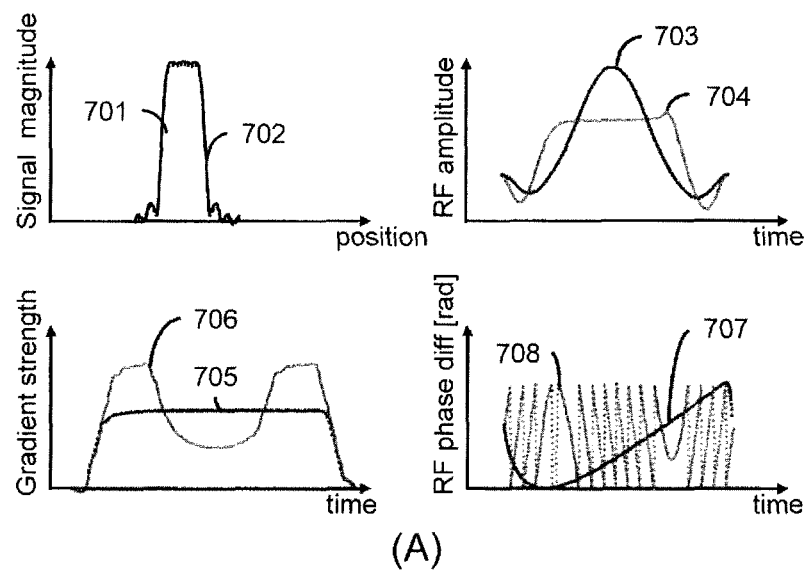
(A)
(B)

MAGNETIC RESONANCE IMAGING APPARATUS AND HIGH-FREQUENCY MAGNETIC FIELD DERTERMINATION METHOD

FIELD OF THE INVENTION

The present invention relates to a nuclear magnetic resonance imaging (MRI) technique which measures nuclear magnetic resonance (NMR) signals from protons in an object to be examined and creates an image of density distribution, relaxation time distribution, and the like of the protons, and in particular to a technique for setting an imaging position and imaging region on the object.

DESCRIPTION OF RELATED ART

In an MRI examination, an MRI apparatus creates an image (performs imaging) of a slice in an arbitrary position (imaging cross-section) in an object which is set in a static magnetic field space. The slice position and slice thickness of an imaging target are determined by a slice selective gradient magnetic field and a high-frequency radiofrequency pulse which excites magnetization of protons. Therefore, only magnetization of protons in a slice of a desired thickness in a desired position can be excited by adjusting the waveform (strength) of the slice selective gradient magnetic field and the irradiation frequency and waveform of the radiofrequency pulse. Hereinafter a radiofrequency pulse for exciting magnetization of protons will be referred to as an excitation RF pulse. Also, the center in the slice thickness direction of a slice in an imaging target will be referred to as a slice position or imaging position.

A slice selective gradient magnetic field is generated and applied by applying an electric current to a gradient magnetic field coil which is incorporated in an MRI apparatus. Generally a linear gradient magnetic field which linearly changes with respect to the application time is used for a slice selective gradient magnetic field. When a linear gradient magnetic field is used for a slice selective gradient magnetic field, an excitation RF pulse in the form of a Sinc function is used to make the excitation profile a rectangle shape.

In high-field magnetization of recent years, an SAR (Specific Absorption Rate) has been recognized as a problem. In order to make an improvement in the SAR, the VERSE (variable rate selective excitation) method has been used in high magnetic field devices, which requires lower excitation power than that of excitation RF pulses in the form of a Sinc function (for example, see Non-patent document 1). In the VERSE method, an excitation RF pulse is applied while changing the application strength of a slice selective gradient magnetic field. At this time, for the slice selective gradient magnetic field, a non-linear gradient magnetic field is used which changes to a non-linear form with respect to the application time. Also, a pulse having the amplitude lower than the Sinc function is used for an excitation RF pulse. Since excitation power is proportional to the square of the amplitude of an excitation RF pulse, lower excitation power is sufficient in the VERSE method compared to the method using a linear gradient magnetic field.

PRIOR ART DOCUMENTS

Non-Patent Documents

Non-patent Document 1: Steven Conolly, Dwight Nishimura and Albert Macovski, "Variable-rate selective excitation" Journal of Magnetic Resonance, 78, 940-458 (1988)

Non-patent Document 2: Peter Latta; "Simple phase method for measurement of magnetic field gradient waveforms" MAGNETIC RESONANCE IMAGING 25, 1272-1276 (2007)

SUMMARY OF INVENTION

Technical Problem

Generally, when an electric current is applied to a gradient magnetic field coil which is placed in a magnetic field space for generating a gradient magnetic field, electromagnetic induction is produced which generates eddy currents. Also, since an inverse current is passed in order to invert polar character of the gradient magnetic field, the gradient magnetic field coil vibrates. Due to such generated eddy currents and vibration, an ideal waveform of a gradient magnetic field (theoretical gradient magnetic field) calculated from imaging parameters is distorted.

Then irradiation frequency of an excitation RF pulses is determined on the basis of the above-mentioned theoretical gradient magnetic field waveform. However, the waveform of a slice selective gradient magnetic field to be actually applied (application gradient magnetic field) is distorted as described above, which causes distortion also in the gradient of the magnetic field to be acquired. With such distortion, an error is generated in the position to be excited, which causes deterioration of image quality. Also, distortion of a gradient magnetic field waveform leads to distortion of the range and the strength of excitation (excitation profile), which further deteriorates the image quality. In particular, a non-linear gradient magnetic field, compared to a linear gradient magnetic field, has a tendency to have a large degree of distortion in a gradient magnetic field waveform which causes profile to be easily damaged, whereby improvement of image quality is difficult.

The objective of the present invention, considering the above-described problems, is to provide a technique for obtaining a high quality image even in a case in which a slice selective gradient magnetic field waveform is distorted due to eddy currents and vibration.

BRIEF SUMMARY OF THE INVENTION

The present invention calculates high-frequency magnetic field information on the basis of an output gradient magnetic field waveform to be applied in accordance with an input gradient magnetic field waveform which is set in a pulse sequence, and the calculated high-frequency magnetic field information is set in the pulse sequence. Then imaging is executed using such pulse sequence in which high-frequency magnetic field information is set.

Effect of the Invention

In accordance with the present invention, it is possible to obtain a high quality image even in a case in which a slice selective gradient magnetic field waveform is distorted due to eddy currents and vibration.

BRIEF DESCRIPTION OF THE DRAWINGS

FIG. 4(A) is a view for explaining a theoretical waveform and a waveform to be actually applied in a case of using a linear gradient magnetic field, and FIG. 4(B) is a view for explaining a theoretical waveform and a waveform to be actually applied in a case of using a non-linear gradient magnetic field.

FIG. 9(A) is a view for explaining simulation results in a case in which a linear gradient magnetic field is used and an excitation RF pulse is used which is set by imaging parameters, and FIG. 9(B) is a view for explaining simulation results in a case in which a linear gradient magnetic field and an excitation RF pulse which is acquired by the method in the embodiment related to the present invention are used.

FIG. 10(A) is a view for explaining simulation result in a case in which a non-linear gradient magnetic field is used and an excitation RF pulse is used which is set based on imaging parameters, and FIG. 10(B) is a view for explaining simulation result in a case in which a non-linear gradient magnetic field is used and an excitation RF pulse is used which is acquired by a method in the embodiment related to the present invention.

FIG. 11(A) is a view for explaining comparison result of excitation RF pulses between a case in which a linear gradient magnetic field is used and a case in which a non-linear gradient magnetic field is used, and FIG. 11(B) is a view for explaining comparison result of images obtained using an excitation RF pulse acquired by the method in the embodiment related to the present invention between a case in which a linear gradient magnetic field is used and a case in which a non-linear gradient magnetic field is used.

DETAILED DESCRIPTION OF THE INVENTION

Figure 1:
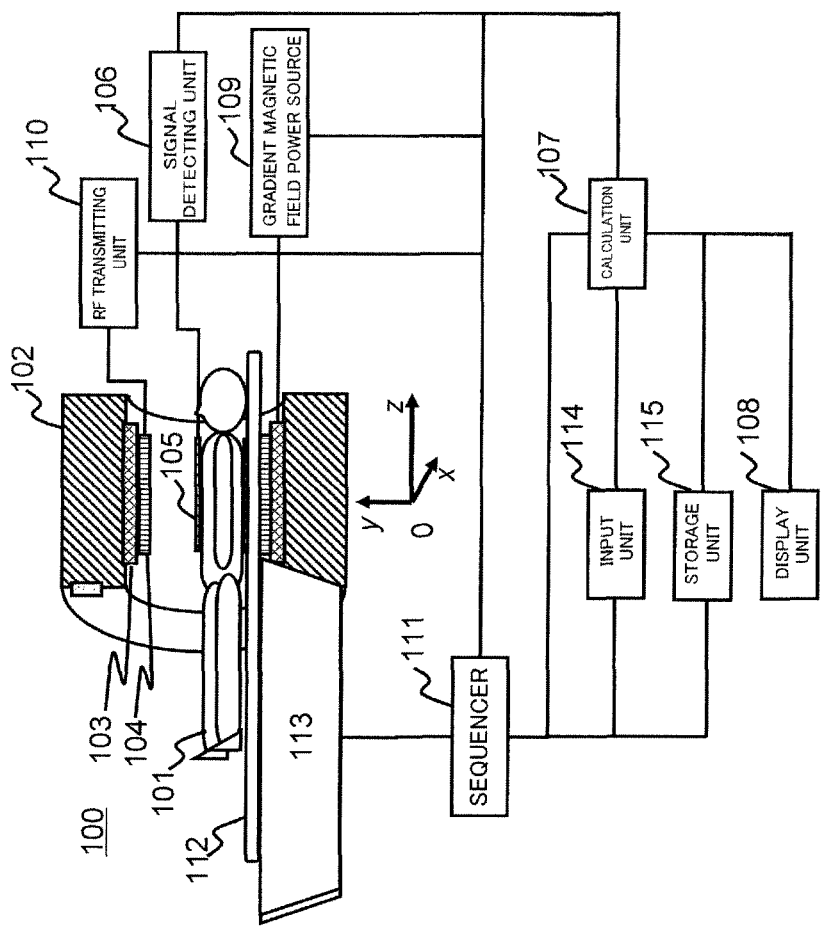
FIG. 1 is a block diagram of an MRI apparatus in an embodiment related to the present invention.

An embodiment of the present invention will be described below. In the following description, the same function parts are represented by the same reference numerals, and the duplicative description thereof will be omitted.

First, an MRI apparatus in the present embodiment will be described referring to FIG. 1. The MRI apparatus 100 in the present embodiment comprises a bed 112 on which an object 101 is placed, a magnet 102 which generates a static magnetic field, a gradient magnetic field coil 103 configured to apply a gradient magnetic field in a static magnetic field space, an RF transmitting coil 104 configured to apply a high frequency magnetic filed to the object 101, an RF receiving coil 105 configured to detect NMR signals produced by the object 101, and a sequencer 111 configured to control operation of the respective components in the MRI apparatus 100.

The bed 112 inserts the object 101 into a static magnetic field space formed by the magnet 102 and carries out the object from the static magnetic field space. The bed 112 is activated by a bed driving unit 113. The bed driving unit 113 controls operation of the bed 112 at least in the body axis direction in accordance with control signals provided by the sequencer 111. In the following description of the present specification, the body-axis is set as z-direction, then among two-directions that are perpendicular to a z-direction, a direction perpendicular to a bed surface is set as a y-direction and the other direction (a direction perpendicular to the z-direction and the y-direction) is set as an x-direction.

The gradient magnetic field coil 103 constitutes a gradient magnetic field system which applies a gradient magnetic field in a static magnetic field space along with the gradient magnetic field power source 109. The gradient magnetic field coil 103 comprises coils which generate a gradient magnetic field in three directions of x, y and z respectively, and applies gradient magnetic fields that are orthogonal to each other by the respective coils to an imaging region. The gradient magnetic field is applied, in response to a signal from the sequencer 111, from the gradient magnetic field power source 109 in accordance with a current to be supplied to the gradient magnetic field coil 103. The respective gradient magnetic fields are used as a slice selective gradient magnetic field which determines an imaging position (imaging slice) in an offset imaging, a phase encoding gradient magnetic field which provides a phase encode, and a readout gradient magnetic field which provides a readout encode. The respective encodes can be set in arbitrary directions. Hereinafter, a slice selective gradient magnetic field for determining an imaging position is referred to as a gradient magnetic field.

The RF transmitting coil 104 constitutes an RF application system which applies a high-frequency magnetic field (excitation RF pulse) to the object 101 along with the RF transmission unit 110. The excitation RF pulse is applied in accordance with signals transmitted from the RF transmitting unit 110 to the RF transmitting coil 104 in accordance with a command from the sequencer 111. The irradiation frequency, phase, and amplitude waveform of an excitation RF pulse to be applied are determined in advance, and set in a pulse sequence. An excitation RF pulse having an irradiation frequency and band width capable of exciting a desired slice thickness in a desired slice position is selected and applied in accordance with the slice selective gradient magnetic field. In this manner, nuclear magnetization of protons in a desired slice thickness at a desired slice position in the object 101 is excited, and an FID (free induction decay) signal or an echo signal is generated.

The RF receiving coil 105 constitutes a signal detecting system which detects echo signals generated from the object 101, along with the signal detecting unit 106. The echo signals are received by the RF receiving coil 105 and detected by the signal detecting unit 106.

The detected signals receive processing such as PFT (fast Fourier transformation) in the calculation unit 107, and converted into image signals. The obtained image is displayed on a display unit 108.

The sequencer 111 controls the gradient magnetic field power source 109, the RF transmitting unit 110, the signal detecting unit 106, the bed driving unit 113 and the display unit 108, in accordance with a command or signals from an input unit 114 and the calculation unit 107. The time chart of the control is generally referred to as a pulse sequence.

The calculation unit 107 receives setting or change of imaging parameters via the input unit 114. Using the received imaging parameters and information such as gradient magnetic field strength stored in a storage unit 115, the calculation unit 107 determines an excitation RF pulse in accordance with a gradient magnetic field to be actually applied at the time of imaging.

The calculation unit 107 further creates a pulse sequence using the determined gradient magnetic field and the excitation RF pulse, and issues a command to the sequencer 111 in accordance with the created pulse sequence.

Figure 2:
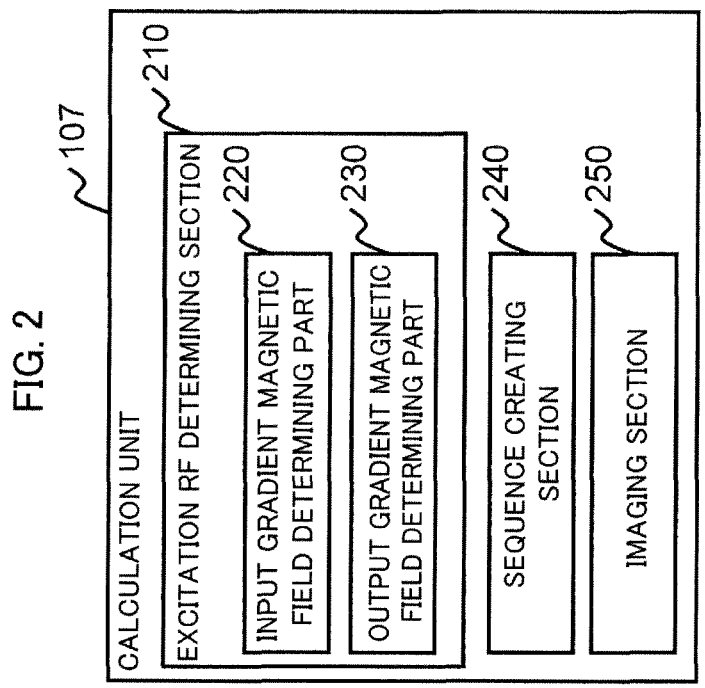
FIG. 2 is a function block diagram of the calculation unit in the embodiment related to the present invention.

In order to carry out the above-described operation, as shown in FIG. 2, the calculation 107 in the present embodiment comprises an excitation RF pulse determining section 210 configured to calculate an excitation RF pulse in accordance with a gradient magnetic field waveform (output gradient magnetic field waveform) to be actually applied at the time of imaging, a sequence creating section 240 configured to reflect the calculated excitation RF pulse to the pulse sequence, and an imaging section 250 configured to perform imaging in accordance with the created pulse sequence.

Also, the excitation RF pulse determining section 210 in the present embodiment determines an output gradient magnetic field waveform by actual measurement using a gradient magnetic field waveform defined by imaging parameters (input gradient magnetic field waveform). For this purpose, the excitation RF pulse determining section 210 comprises an input gradient magnetic field determining part 220 configured to determine an input gradient magnetic field waveform from imaging parameters and an output gradient magnetic field determining part 230 configured to determine a gradient magnetic field waveform to be actually applied at the time of imaging (output gradient magnetic field waveform) from the determined input gradient magnetic field waveform.

Figure 3:
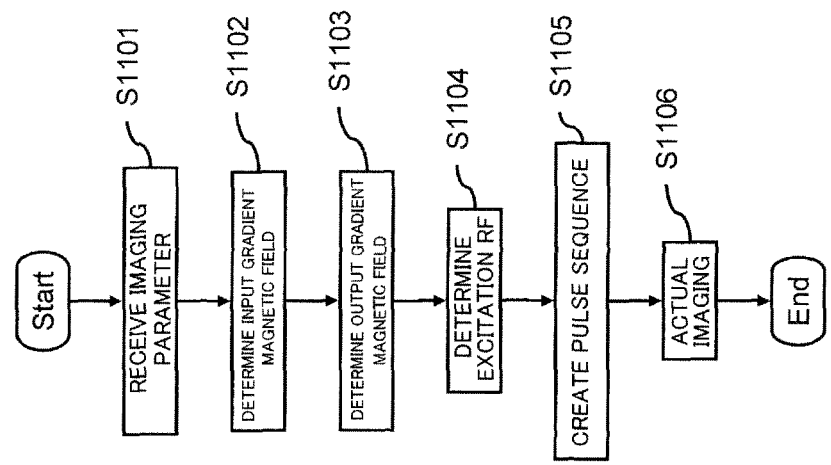
FIG. 3 is a flowchart showing processes at the time of imaging in the embodiment related to the present invention.

First, the outline of processing flow by the calculation unit 107 at the time of imaging will be described using the flowchart shown in FIG. 3.

An operator first sets imaging parameters via the input unit 114. In response to the input, the calculation unit 107 receives imaging parameters (step S1101). Next, the input gradient magnetic field determining part 220 determines input gradient magnetic field waveform Gs_in(t) on the basis of the imaging parameters (input gradient magnetic field determining process: step S1102). Then the output gradient magnetic field determining part 230 determines output gradient magnetic field waveform Gs_out(t) to be actually applied at the time of imaging on the basis of imaging parameters and the calculated input gradient magnetic field waveform (output gradient magnetic field determining process: step S1103). Next, the excitation RF pulse determining section 210 determines an excitation PT pulse on the basis of imaging parameters and the determined output gradient magnetic field waveform (excitation RF pulse determining process: step S1104).

Then the sequence creating section 240 creates a pulse sequence to which the input imaging parameters and determined excitation RF pulse are reflected (step S1105). The imaging section 250 activates the respective components and executes imaging in accordance with the created pulse sequence (step S1106). That is, at a time of imaging, the imaging section 250 irradiates the determined excitation RF pulse from the RF transmitting coil 104.

The process of each step from step S1102 to step S1104 will be described below in detail.

First, the input gradient magnetic field determining process by the input gradient magnetic field determining part 220 in step 1102 will be described.

The input gradient magnetic field determining part 220 calculates a preset theoretical gradient magnetic field waveform of a gradient magnetic field. A linear gradient magnetic field or non-linear magnetic field is to be used for the gradient magnetic field. Here, a case in which a linear gradient magnetic field is used will be described as an example.

Since gradient magnetic field strength in a gradient magnetic field of a general linear magnetic field is constant regardless of an application time of the gradient magnetic field, a theoretic waveform thereof is indicated as shown in 504 of FIG. 4(A). FIG. 4(A) is a graph showing the time change of gradient magnetic field strength (Gradient strength). At this time, gradient magnetic field strength Gs_flat(t) of a flat portion 504f is acquired by the following equation (1).

$$Gs\_flat(t) = TBW/(\gamma \cdot zw \cdot D) \qquad (1)$$

Here, TBW (time-bandwidth) is the number of times wherein the strength of an exciting RF pulse becomes 0 in an excitation RF pulse. This is a known value which is determined for each RF pulse waveform to be used for an excitation RF pulse. $\gamma$ is the magnetogyric ratio. zw is the slice thickness, and is given also as an imaging parameter. D is an application time, and is equal to the excitation time of an excitation RF pulse. Since a rising portion 504u and a falling portion 504d are not related to an excitation pulse, gradient magnetic field strength Gs_flat(t) of the flat portion 504f is set as input gradient magnetic field waveform Gs_in(t) for ease of explanation.

When a non-linear gradient magnetic field is used for a gradient magnetic field, the gradient magnetic field strength is changed corresponding to the application time of the gradient magnetic field. The theoretic waveform of a non-linear gradient magnetic field is as shown in 604 of FIG. 4(B). The detailed calculation method of the theoretical waveform 604 is as disclosed in Non-patent Document 1.

That is, gradient magnetic field waveform Gs_in(t) in a case of a non-linear gradient magnetic field can be expressed by the following equation (2).

$$Gs\_in(t) = Gs\_linear(t) \times vRF(t)/oRF(t) \qquad (2)$$

Here, Gs_linear(t) is a gradient magnetic field waveform of a linear gradient magnetic field, vRF(t) is an excitation RF pulse waveform corresponding to a non-linear gradient magnetic field, and oRF(t) is an excitation RF pulse waveform corresponding to a linear gradient magnetic field. Also, vRF(t) is created by raising the amplitude of both sides so that the maximum amplitude becomes $\alpha$ times the value of the maximum amplitude of oRF(t) without changing the area and irradiation time of oRF(t). In this regard, however, the value of $\alpha$ is to be 1 or smaller and should not surpass the slew rate of the slice selective gradient magnetic field. In FIG. 4(B), an output gradient magnetic field waveform is indicated by 605.

Next, an output gradient magnetic field determining process by the output gradient magnetic field determining part 230 in step S1103 will be described.

The output gradient magnetic field waveform Gs_out(t) is distorted due to eddy currents and vibration as described above, and turns out as shown in 505 of FIG. 4(A). The present embodiment calculates an output gradient magnetic field waveform using the technique disclosed in Non-patent document 2. The technique in Non-patent Document 2 executes pulse sequences with and without the application of a gradient magnetic field during acquisition of signals, and acquires the gradient magnetic field application amount for each unit time from the variation per unit time in the phase difference in each of the signal strengths. By comparing such acquired application amount with an application amount of the theoretical gradient magnetic field, the amount of distortion can be grasped. In this manner, the output gradient magnetic field determining part 230 of the present embodiment calculates and determines output gradient magnetic field waveform 505Gs_out(t) by executing a gradient magnetic field waveform calculating sequence. This gradient magnetic field waveform calculating sequence is executed in prior to an actual imaging.

Figure 5:
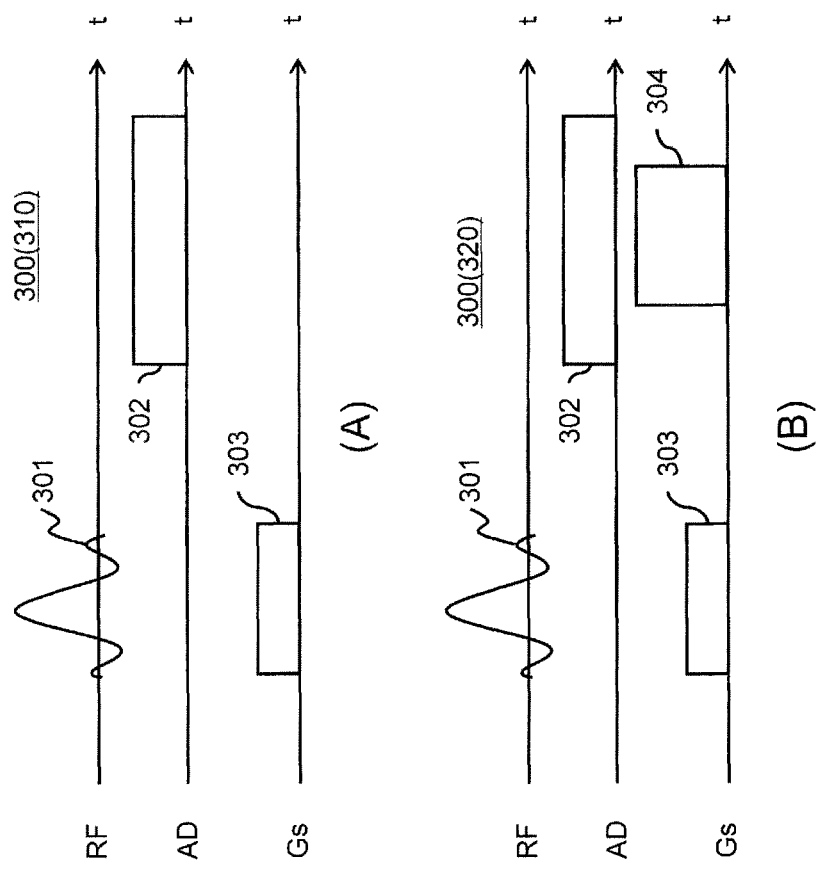
FIGS. 5(A) and (B) are views for explaining a gradient magnetic field waveform calculating sequence in the embodiment related to the present invention.

A gradient magnetic field waveform calculating sequence 300 is shown in FIG. 5(A) and FIG. 5(B). In these diagrams, RF indicates timing of an RF pulse application, AD indicates timing of data acquisition, and Gs indicates application timing of a slice gradient magnetic field.

The gradient magnetic field waveform calculating sequence 300 comprises a first pulse sequence 310 shown in FIG. 5(A) and a second pulse sequence 320 shown in FIG. 5(B). The first pulse sequence 310 and the second pulse sequence 320 are provided with an RF pulse 301 and a slice selective gradient magnetic field 303 to be applied simultaneously with the RF pulse 301.

After applying the RF pulse 301 and the slice selective gradient magnetic field 303, the first pulse sequence 310 executes data acquisition 302 without applying a slice gradient magnetic field. On the other hand, the second pulse sequence executes the data acquisition 302 while applying a second slice selective gradient magnetic field 304. The second slice selective gradient magnetic field 304 is set as a gradient magnetic field waveform 504Gs_in(t) which is the same as the slice selective gradient magnetic field (input gradient magnetic field) to be used in the actual imaging. In other words, it is the gradient magnetic field to be specified by the imaging parameter which is the same as the slice selective gradient magnetic field to be used in the actual imaging.

The output gradient magnetic field determining part 230 in the present embodiment executes the first pulse sequence 310 and the second pulse sequence 320. Then, using the first echo signal acquired by the first pulse sequence 310 and the second echo signal acquired by the second pulse sequence 320, the phase variation in the echo signals caused by the difference between the presence and absence of the second slice selective gradient magnetic field 304 is obtained.

Variation of the phase in echo signals caused by the difference between the presence and absence of the second slice selective gradient magnetic field 304 in unit time Δt is known as being the same as the application amount of the relevant gradient magnetic field in the unit time. Using this, the output gradient magnetic field determining part 230 acquires the time variation in application amount of the second slice selective gradient magnetic field 304, i.e. output gradient magnetic field waveform 505Gs_out(t) of the slice selective gradient magnetic field to be used for the actual imaging.

Next, an excitation RF pulse determining process by the excitation RF pulse determining section 210 in the above-described step S1104 will be described.

An excitation RF pulse can be expressed by the following equation (3).

$$RF = RFa(t) \cdot \exp(j2\pi \cdot RFf \cdot t + RFp(t)) \quad (3)$$

Here, RFa(t) is the pulse waveform (amplitude waveform) of an excitation RF pulse, RFp(t) is the phase of the excitation RF pulse, RFf is the irradiation frequency of the excitation RF pulse, j is the imaginary unit, and · is the multiplication sign.

Figure 6:
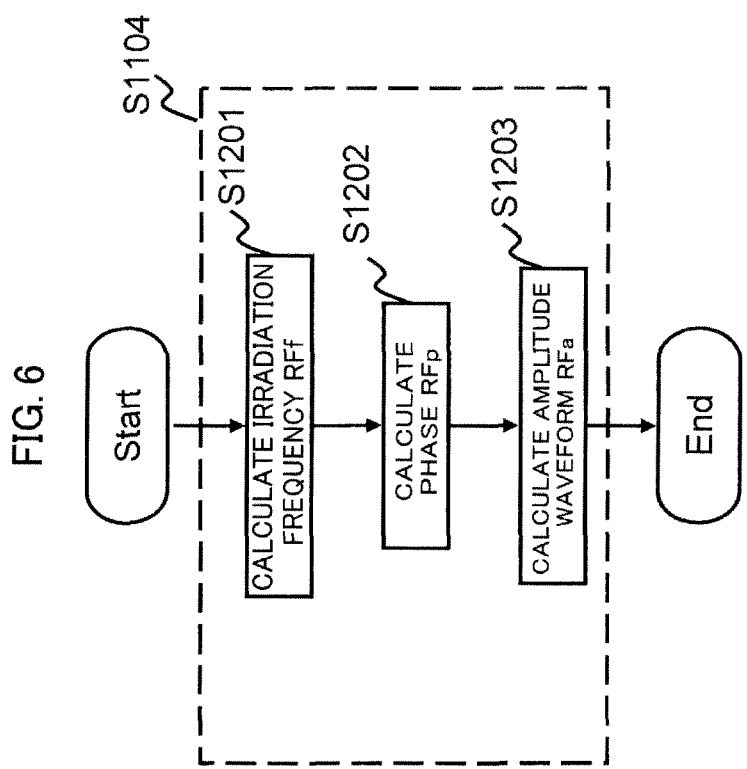
FIG. 6 is a flowchart showing an excitation RF pulse determining process in the embodiment related to the present invention.

In the present embodiment, the excitation RF pulse determining section 210 calculates the irradiation frequency RFf, phase RFp(t) and amplitude waveform RFa(t) of an excitation RF pulse, and determines the excitation RF pulse. As shown in FIG. 6, the excitation RF pulse determining section 210 first calculates irradiation frequency RFf using output gradient magnetic field waveform Gs_out(t) (irradiation frequency RFf calculating process: step S1201). Then the excitation RF pulse determining section 210 calculates the amount of phase variation which is caused when an applied gradient magnetic field changed from an input gradient magnetic field waveform to an output gradient magnetic field waveform as phase RFp(t) (phase RFp calculating process: step S1202). Finally, the excitation RF pulse determining section 210 calculates amplitude waveform RFa(t) of the excitation RF pulse using output gradient magnetic field waveform Gs_out(t) and input gradient magnetic field waveform Gs_out(t) (amplitude RFa calculating process: step S1203).

First, the irradiation frequency RFf calculating process of the above-described step S1201 will be described in detail. An irradiation frequency RFf of an excitation RF pulse is generally calculated by the following equation (4) using strength Gs of the slice selective gradient magnetic field and imaging position Z.

$$RFf = \gamma \cdot (Gs \cdot Z) + \gamma \cdot B0 \quad (4)$$

Here, γ is the magnetogyric ratio, and B0 is the static magnetic field strength.

The excitation RF pulse determining section 210 in the present embodiment calculates the irradiation frequency RFf of the excitation RF pulse by the following equation (5) using average value Ave(Gs_out(t)) in the time direction Gs_out(t) for the slice selective gradient magnetic field strengths Gs of the above-mentioned equation (4).

$$RFf = \gamma \cdot Ave(Gs\_out(t)) \cdot OD \quad (5)$$

Here, OD is the imaging position expressed by the distance from the center of a magnetic field (offset distance: OD). The offset distance OD is to be input by a user. Imaging in which an imaging position is not set at the center of the magnetic field, i.e. imaging of which the offset distance is not 0 is referred to as offset imaging.

Next, a phase RFp calculating process of the above-described step S1202 will be described in detail. Here, the excitation RF pulse determining section 210 calculates the phase variation caused by distortion of a gradient magnetic field as phase RFp(t) of the excitation RF pulse as described above. When there is no distortion in the gradient magnetic field, phase RFp of the excitation RF pulse is set as 0.

Figure 7:
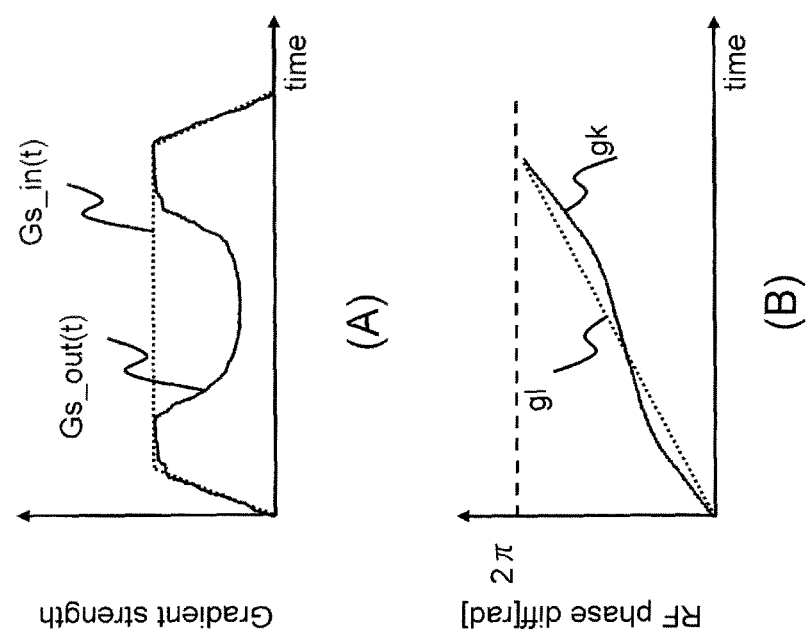
FIG. 7(A) is a view for explaining an input gradient magnetic field waveform and an output gradient magnetic field waveform in the embodiment related to the present invention.
FIG. 7(B) is a view for explaining phase variation by an input gradient magnetic field and phase variation by an output gradient magnetic field in the embodiment related to the present invention.

When a gradient magnetic field waveform has a theoretical pattern as shown in input gradient magnetic field waveform Gs_in(t) of FIG. 7(A), the phase linearly changes from 0 to 2 π in one cycle as shown in gl(t) of FIG. 7(B). On the other hand, when a gradient magnetic field waveform is distorted as shown in output gradient magnetic field waveform Gs_out(t) of FIG. 7(A), the phase in one cycle changes as shown in gk(t) of FIG. 7(B). Here, gk(t) is standardized so that the maximum value of the cumulative sum of phases becomes 2π. Also, FIG. 7(A) is a graph showing the time change in gradient magnetic field strength (Gradient strength), and FIG. 7(B) is a graph showing the time change in phase variation (RF Phase diff).

Therefore, phase RFp(t) can be expressed by the following equation (6).

$$RFp(t)=(gk(t)-gl(t))\cdot RFfD \qquad (6)$$

Here, D is the application time of a gradient magnetic field and excitation RF pulse.

As described above, phase RFp of an excitation RF pulse is set as 0 here when there is no distortion in the gradient magnetic field. However, when an excitation RF pulse has a phase other than the phase variation due to the gradient magnetic field, the phase value is to be added to RFp as need arises.

Next, an amplitude waveform RFa calculating process in the above-described step S1203 will be described in detail. Pulse waveform RFa(t) of an excitation RF pulse is designed so that the range to be excited (cross-section of the slice thickness (thickness of an imaging region): referred to as an excitation profile) becomes a rectangle. An excitation profile is a Fourier-transformed pulse waveform of an excitation RF pulse. In order to acquire a rectangle-shaped excitation profile, for example, a sinc function waveform is used for pulse waveform RFa(t) of an excitation RF pulse.

When an excitation RF pulse waveform which is designed by assuming that a gradient magnetic field to be applied is input gradient magnetic field waveform Gs_in(t) is set as RFa_in(t), amplitude waveform RFa(t) of an excitation RF pulse to be used can be expressed by the following equation (7).

$$RFa(t)=RFa\_in(t)\cdot Gs\_out(t)/Gs\_in(t) \qquad (7)$$

Here, excitation RF pulse waveform RFa_in(t) is calculated by the slice thickness and bandwidth that are provided as imaging parameters.

As described above, the excitation RF pulse determining section 210 determines an excitation RF pulse by calculating irradiation frequency RFf and phase RFp(t) of the excitation RF pulse.

Figure 8:
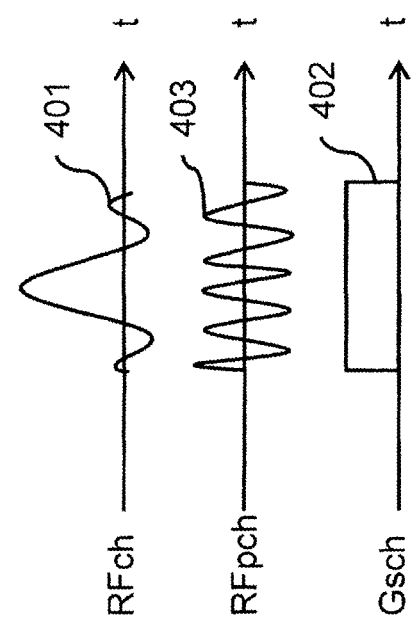
FIG. 8 is a view for explaining a pulse sequence to be created by a sequence creating section in the embodiment related to the present invention.

Next, a pulse sequence creating process by the sequence creating section 240 of step S1105 will be described. The sequence creating section 240 creates a pulse sequence so that an excitation RF pulse having the irradiation frequency RFf, phase RFp(t) and amplitude waveform RFa(t) that are calculated as above is applied at the time of imaging. In concrete terms, as shown in FIG. 8, an excitation RF pulse 401 in which the above-mentioned irradiation frequency RFf is phase-modulated as a modulating frequency is set in RFch, and the calculated phase RFp(t) 403 is set in RFpch. The waveform of the excitation RF pulse 401 is set as RFa(t). In addition, an input gradient magnetic field waveform Gs_in(t) 402 which is calculated from imaging parameters is set in gradient magnetic field GSch.

The imaging section 250 executes imaging in accordance with the acquired pulse sequence.

Here, the simulation result showing the effect of the present embodiment is shown in FIG. 9 and FIG. 10. In the present simulation, the offset from the magnetic field center in an imaging position is set as 60 mm.

FIG. 9 shows examples in which a linear gradient magnetic field is used for a slice selective gradient magnetic field. FIG. 9(A) is en example of a case in which an excitation RF pulse set by an imaging parameter is used as it is, and FIG. 9(B) is an example of a case in which an excitation RF pulse determined by the above-described embodiment is used.

Each graph in FIG. 9(A) and FIG. 9(B) respectively shows the changing pattern of signal strength (Signal magnitude) in accordance with the position, time change of gradient magnetic field strength (Gradient strength), time change of an amplitude waveform of an excitation RF pulse (RF amplitude), and time change of phases in an excitation RF pulse (RF phase diff).

Input gradient magnetic field waveform Gs_in(t) calculated from imaging parameters is denoted by 504, and output gradient magnetic field waveform Gs_out(t) applied is denoted by 505. Waveform RFa_in(t) of a set excitation RF pulse is denoted by 503, and the phase is denoted by 506. An excitation profile (slice profile) of a case in which the slice selective gradient magnetic field is input gradient magnetic field waveform Gs_in(t) 504 denoted by 501. The excitation RF pulse 503 is designed to make the center thereof to be at an imaging position 510.

However, the slice selective gradient magnetic field to be actually applied has output gradient agnetic field waveform Gs_out(t) 505. For this reason, if a designed excitation RF pulse (the amplitude waveform is 503 and the phase is 506) is used as it is, the slice profile to be acquired becomes as indicated by 502 and the imaging position is displaced as indicated by 511.

On the other hand, as shown in FIG. 9(B), when an excitation RF pulse determined by the method of the present embodiment (amplitude waveform RFp(t) is 508 and phase RFp(t) is 509) is used, the acquired slice profile turned out as indicated by 507 which was approximately overlapped with the excitation profile 501. Therefore, the imaging position also becomes approximately the same as 510. In this manner, it is found that a desired imaging slice can be excited with high accuracy without displacement in the excitation profile itself and displacement in the imaging position, by determining an excitation RF pulse using the method of the present embodiment.

An example in which a non-linear gradient magnetic field is used for a slice selective gradient magnetic field is shown in FIG. 10. FIG. 10(A) is an example of a case in which an excitation RF pulse set by an imaging parameter is used as it is. FIG. 10(B) is an example of a case in which an excitation RF pulse determined by the above-described embodiment is used.

Each graph in FIG. 10(A) and FIG. 10(B) shows respectively the changing pattern of signal strength (Signal magnitude) in accordance with the position, time change of gradient magnetic field strength (Gradient strength), time change of an amplitude waveform of an excitation RF pulse (RF amplitude), and time change of phases in an excitation RF pulse (RF phase diff).

Input gradient magnetic field waveform Gs_in(t) calculated from imaging parameters denoted by 604, and an actually applied output gradient magnetic field waveform Gs_out(t) is denoted by 605. The waveform of set excitation RF pulse Rha_in(t) is denoted by 603, and the phase is denoted by 606. An excitation profile (slice profile) of a case in which the slice selective gradient magnetic field is input gradient magnetic field waveform Gs_in(t) 604 is denoted by 601. The excitation RF pulse 603 is designed to make the center 610 thereof to be at an imaging position.

However, the slice selective gradient magnetic field to be actually applied has output gradient magnetic field waveform Gs_out(t) 605. For this reason, if a designed excitation RF pulse (the amplitude waveform is 603 and the phase is 606) is used as it is, the slice profile to be acquired becomes as indicated by 602 and the imaging position is displaced as indicated by 611.

On the other hand, as shown in FIG. 10(B), when an excitation RF pulse determined by the method in the present embodiment (amplitude waveform RFa(t) is 608 and phase RFp(t) is 609) is used, an acquired slice profile turned out as indicated by 607 which was approximately overlapped with the excitation profile 601. Thus, the imaging position also becomes approximately the same as 610.

In this manner, it is found that a desired imaging slice can be excited with high accuracy without displacement in the profile itself and the imaging position, by determining an excitation RF pulse using the method of the present embodiment.

As described above, in accordance with the present embodiment, an excitation RF pulse is determined in accordance with an actually applied output gradient magnetic field waveform at the time of imaging. In other words, irradiation frequency RFf and phase RFp(t) are determined based on an actually applied gradient magnetic field waveform Gs_out(t). Therefore, even when a gradient magnetic field changes from input gradient magnetic field waveform Gs_in(t) to output gradient magnetic field waveform Gs_out(t), a desired slice position can be excited. Also, amplitude waveform RFa(t) is determined in the same manner. Therefore, even when a gradient magnetic field changes from input gradient magnetic field Gs_in(t) to output gradient magnetic field Gs_out(t), an excitation profile of a desired pattern can be acquired, whereby a desired slice thickness can be excited as a result.

As described above, in accordance with the present embodiment, even when distortion is generated in an actually applied slice selective gradient magnetic field waveform due to eddy currents and vibration, an excitation RF pulse can be irradiated having the frequency, phase and amplitude waveform that are appropriate for a slice selective gradient magnetic field to be actually applied. As a result, a desired slice can be excited with high accuracy and the image quality can be improved.

Here, in a case in which an excitation RF pulse is determined by the method in the present embodiment, comparison results between an example in which a linear gradient magnetic field is used and an example in which a non-linear gradient magnetic field for a slice selective gradient magnetic field is used are shown in FIG. 11(A) and FIG. 11(B). The other imaging conditions are assumed to be the same. The graphs in FIG. 11(A) respectively indicate the changing pattern of signal strength (Signal magnitude) in accordance with the position, time change of gradient magnetic field strength (Gradient strength), time change of amplitude pattern in an excitation RF pulse (RF amplitude), and time change of the phase in the excitation RF pulse (RF phase diff).

In a case in which a linear gradient magnetic field 705 is used for a slice selective gradient magnetic field, amplitude waveform RFa(t) of an excitation RF pulse which is determined by the method of the present embodiment is indicated by 703, phase variation RFp(t) is indicated by 707, and the excitation profile (slice profile) is indicated by 701. Also, such obtained image is shown in 709 of FIG. 11(B).

Also, in a case in which a nonlinear gradient magnetic field 706 is used for a slice selective gradient magnetic field, amplitude waveform RFa(t) of an excitation RF pulse which is determined by the method of the present embodiment is indicated by 704, phase variation RFp(t) is indicated by 708, and the excitation profile (slice profile) is indicated by 702. Then, such obtained image is shown in 710 of FIG. 11(B).

As shown in FIG. 11(A), the waveforms and imaging positions of the slice profile 701 and the slice profile 702 approximately coincide with each other. Also, the image 709 and the image 710 have approximately the same image quality as shown in FIG. 11(B). However, when the amplitude waveforms 703 and 704 are compared, the value of the amplitude waveform 704 is smaller than that of the amplitude waveform 703 and requires lower RF excitation power. Therefore, the comparison result shows that, under the same imaging condition, an image having the same image quality can be obtained with a lower excitation power by using a non-linear gradient magnetic field iota slice selective gradient magnetic field.

In this manner, in accordance with the present embodiment, it is possible to irradiate an excitation RF pulse having the frequency, phase and amplitude waveform that are determined on the basis of an actually applied gradient magnetic field waveform, even when a non-linear gradient magnetic field is used for a slice selective gradient magnetic field. Therefore, a desired slice can be excited in the same manner as a case in which a linear gradient magnetic field is used for a slice selective gradient magnetic field.

Conventionally, more degradation of image quality had occurred when a non-linear magnetic field is used compared to a case of using a linear magnetic field under the same condition, due to a large amount of distortion generated in the magnetic field which leads to damage of the excitation profile. However, in accordance with the present embodiment, the same image quality can be acquired when using either a linear gradient magnetic field or a non-linear gradient magnetic field for a slice selective gradient magnetic field. Therefore, lower excitation power consumption can be achieved for acquiring the same image quality.

In the above-described embodiment, the output gradient magnetic field determining part 230 determines output gradient magnetic field waveform Gs_out(t) for each actual imaging by executing a gradient magnetic field waveform calculating sequence based on a slice selective gradient magnetic field waveform (input gradient magnetic field waveform; Gs_in(t)) to be used for an actual imaging. However, the method for determining output gradient magnetic field waveform Gs_out(t) is not limited thereto.

Gradient magnetic field strength is inversely proportional to the slice thickness. Therefore, for example, output gradient magnetic field waveform Gs_out(t) in an actual imaging in which only the slice thickness is different from the imaging wherein the output gradient magnetic field waveform Gs_out(t) is obtained by the above-described method can be calculated by the following equation (8) without executing the gradient magnetic field waveform calculating sequence 300.

$$Gs\_out(t) = c \cdot Tb \cdot Gsb(t)/Tg \quad (8)$$

Here, Gsb(t) is a gradient magnetic field waveform to be the base, which is calculated by executing the above-mentioned gradient magnetic field waveform calculating sequence 300, and Tb is the slice thickness at that time. On the other hand, Tg is the slice thickness in an actual imaging for calculating output gradient magnetic field waveform Gs_out(t). Also, c is a correlation coefficient. The correlation coefficient c is to be obtained in advance by calculating the output gradient magnetic field waveforms with two or more different slice thicknesses respectively by executing the above-described gradient magnetic field waveform calculating sequence 300.

Also, output gradient magnetic field waveform Gs_out(t) may also be determined by calculating with use of a system transfer function ts(t) which is inherent in the MRI apparatus 100. That is, output gradient magnetic field waveform Gs_out(t) can be calculated by the following equation (9) using input gradient magnetic field waveform Gs_in(t) and system transfer function ts(t).

$$Gs\_out(t) = \int_0^t Gs\_in(\tau) \cdot ts(t-\tau) d\tau \quad (9)$$

Here, t is the application time of a slice selective gradient magnetic field, $\tau$ is the variable which satisfies $0 \leq \tau \leq t$. Also, system transfer function ts(t) is a response function which attenuates temporally, and has plural time constants and gains due to attributes such as eddy currents. As for a response function which can be used as system transfer function ts(t), for example, the exponential function expressed by the following equation (10) can be used.

$$ts(t) = g_1 \cdot \exp\left(-\frac{t}{\tau_1}\right) + g_2 \cdot \exp\left(-\frac{t}{\tau_2}\right) + g_3 \cdot \exp\left(-\frac{t}{\tau_3}\right) \quad (10)$$

Here, $g_1$, $g_2$ and $g_3$ are the gains, and $\tau_1$, $\tau_2$ and $\tau_3$ are the time constants. The values of these gains and time constants are dependent on an apparatus, thus measurement of these values is required only one time such as the time of installation for each MRI apparatus.

The gains and time constants of system transfer function ts(t) are not limited to those acquired by measurements. For example, the optimal value may also be determined while changing the gain and the time constant. In this case, candidate Gs_app(t) of output gradient magnetic field waveform Gs_app(t) is calculated using the above-described equation (9) and equation (10) each time the gain and time constant are changed, the calculated candidate is compared with gradient magnetic field waveform Gsb(t) to be the base which is calculated by executing the gradient magnetic field waveform calculating sequence 300, and the gain and time constant which are most approximated thereto are applied. The degree of similarity between output gradient magnetic field waveform candidate Gs_app(t) and gradient magnetic field waveform Gsb(t) to be the base is evaluated using the minimum squares of sum which is indicated in the following equation (11).

$$lsm = \sum_{\tau=0}^{t} (gs\_app(\tau) - Gsb(\tau))^2 \quad (11)$$

Further, the gain and time constant in the equation (10) may also be calculated after performing the Laplace transformation or z transformation with respect to the equation (9).

While output gradient magnetic field waveform determining part 230 is configured to calculate output gradient magnetic field waveform Gs_out(t) with respect to input gradient magnetic field waveform Gs_in(t) for each actual imaging or each time that an imaging parameter is changed in the above-described embodiment, the calculation method is not limited thereto. Any method may be used which can calculate output gradient magnetic field waveform Gs_out(t) with respect to input gradient magnetic field waveform Gs_in(t) which is determined by an imaging parameter.

For example, output gradient magnetic field waveform Gs_out(t) with respect to input gradient magnetic field waveform in_out (t) is stored in the storage unit 115 as database for each representative imaging parameter. Then, the output gradient magnetic field determining part 230 may be configured to extract the output gradient magnetic field waveform Gs_out(t) stored in the database by corresponding to the input gradient magnetic field waveform Gs_in(t) in accordance with the imaging parameter for each imaging, instead of calculating the output gradient magnetic field waveform Gs_out(t).

In addition, while an example of an orthogonal cross-section imaging in which an imaging cross-section is parallel to any of the xy-plane, yz-plane and zx-plane is described in the embodiment above, the imaging is not limited thereto. For example, oblique imaging may also be applied which is cross-sectional imaging in an arbitrary angle. Output gradient magnetic field waveform Gs_out(t) in a case of oblique imaging can be expressed by the following equation (12).

$$Gs\_out(t) = \sqrt{(wx \cdot G\_x(t))^2 + (wy \cdot G\_y(t))^2 + (wz \cdot G\_z(t))^2} \quad (12)$$

Here, G_x(t), G_y(t) and G_z(t) are output gradient magnetic field waveforms in the x-axis, y-axis and z-axis directions respectively, and wx, wy and wz are the weights in accordance with an oblique angle. The weight can be calculated by the rotating coordinates and the oblique angle set by a user. It is preferable that they are stored in the storage unit 115 in advance.

Output gradient magnetic field waveforms G_x(t), G_y(t) and G_z(t) in the x-axis, y-axis and z-axis directions are to be calculated using any of the above-described methods.

Also, while the excitation RF pulse determining section 210 calculates irradiation frequency RFf and phase variation RFp(t) of an excitation RF pulse from obtained output gradient magnetic field waveform Gs_out(t) in the above-described embodiment, the calculation method is not limited thereto. They also may be calculated by modifying irradiation frequency RFf_in and phase RFp_in (t) of the excitation RF pulse determined for each sequence. The irradiation frequency RFf_in and phase RFp_in(t) are calculated from a theoretical gradient magnetic field, i.e. input gradient magnetic field waveform Gs_in(t).

Correction amount $\Delta$RFf of irradiation RFf and correction amount $\Delta$RFp(t) of phase RFp(t) in this case can be expressed by the following equations (13) and (14) respectively.

$$\Delta RFf = \gamma \cdot (Ave(Gs\_in(t)) - Ave(Gs\_out(t))) \cdot OD \quad (13)$$

Here, Ave(Gs_in(t)) is the average value of input gradient magnetic field waveforms Gs_in(t) in the time direction, and Ave(Gs_out (t)) is the average value of output gradient magnetic field waveforms Gs_out(t) in the time direction.

$$\Delta RFp(t) = (gcal(t) - gk(t)) \cdot RFf \cdot D \quad (14)$$

Here, gcal(t) is the variation of the phase per cycle caused by input gradient magnetic field waveform Gs_in (t), which is standardized to make the maximum position to be $2\pi$.

Then, irradiation frequency RFf and phase RFp(t) can be calculated by the following equations (15) and (16) respectively.

$$RFf = RFf\_in + \Delta RFf \quad (15)$$

$$RFp(t) = RFp\_in(t) + \Delta RFp(t) \quad (16)$$

Also, while the process of determining an excitation RF pulse in accordance with input gradient magnetic field waveform Gs_in(t) is executed by the calculation unit 107 provided in the MRI apparatus 100 in the present embodiment, the configuration is not limited thereto. For example, an excitation RF pulse may also be determined in accordance with input gradient magnetic field waveform Gs_in(t) in an information processing device which is separate from the MRI apparatus 100 and is capable of transmitting/receiving data to/from the MRI apparatus 100.

DESCRIPTION OF REFERENCE NUMERALS

100: MRI apparatus, 101: object, 102: magnet, 103: gradient magnetic field coil, 104: RF transmitting coil, 105: RF receiving coil, 106: signal detecting unit, 107: calculation unit, 108: display unit, 109: gradient magnetic field power source, 110: RF transmitting unit, 111: sequencer, 112: bed, 113: bed driving unit, 114: input unit, 115: storage unit, 210: excitation RF pulse determining section, 220: input gradient magnetic field determining part, 230: output gradient magnetic field determining part, 240: sequence creating section, 250: imaging section, 300: gradient magnetic field waveform calculating sequence, 301: RF pulse, 302: data acquisition, 303: slice selective gradient magnetic field, 304: slice selective gradient magnetic field, 310: pulse sequence, 320: pulse sequence, 401: excitation RF pulse, 402: input gradient magnetic field waveform, 403: phase, 501: excitation profile, 502: excitation profile 503, amplitude waveform, 504: input gradient magnetic field waveform, 504d: falling portion, 504f: flat portion, 504u: rising portion, 505: output gradient magnetic field waveform, 506: phase, 507: excitation profile, 508: amplitude waveform, 509: phase, 510: imaging position, 511: imaging position, 601: excitation profile, 602: excitation profile, 603: amplitude waveform, 604: input gradient magnetic field waveform, 605: output gradient magnetic field waveform, 606: phase, 607: excitation profile, 608: amplitude waveform, 609: phase, 610: imaging position, 611: imaging position, 701: slice profile, 702: slice profile, 703: amplitude waveform, 704: amplitude waveform, 705: linear gradient magnetic field, 706: non-linear gradient magnetic field, 707: phase, 708: phase, 709: image, 710: image.

The invention claimed is:

1. A magnetic resonance imaging apparatus comprising:
a magnet which generates a static magnetic field;
a gradient magnetic field generating unit configured to apply a gradient magnetic field in a static magnetic field space;
a high-frequency magnetic field applying unit configured to apply a high-frequency magnetic field to an object to be examined;
a signal detecting unit configured to detect a nuclear magnetic resonance signal generated from the object;
a measurement control unit configured to control operation of the gradient magnetic field generating unit, the high-frequency magnetic field applying unit and the signal detecting unit; and
a calculation unit configured to issue a command to the measurement control unit to control in accordance with a predetermined pulse sequence and perform calculation including reconstruction of an image from nuclear magnetic resonance signals detected by the signal detecting unit,
wherein the calculation unit comprises:
a high-frequency magnetic field determining unit configured to determine high-frequency magnetic field information to be applied from the high-frequency magnetic field applying unit on the basis of an output gradient magnetic field waveform which is applied by the gradient magnetic field generating unit in accordance with an input gradient magnetic field waveform which is input according to the pulse sequence; and a sequence creating unit configured to set high-frequency magnetic field information determined by the high-frequency magnetic field determining unit in the pulse sequence, and
wherein the calculation unit is configured to calculate a correction amount in a frequency of the high-frequency magnetic field and a correction amount in a phase of the high-frequency magnetic field, and determines the high-frequency magnetic field information to be set in the pulse sequence by correcting the frequency and phase of a preset high-frequency magnetic field using the correction amounts.

2. The magnetic resonance imaging apparatus according to claim 1, wherein:
the calculation unit is configured to calculate irradiation frequency of the high-frequency magnetic field using the output gradient magnetic field waveform and is configured to calculate the phase variation caused by the change of an applied gradient magnetic field from the input gradient magnetic field waveform to the output gradient magnetic field waveform; and
the sequence creating unit sets the calculated phase variation in the high-frequency magnetic field information of the pulse sequence.

3. The magnetic resonance imaging apparatus according to claim 2, wherein:
the calculation unit calculates the frequency of the high-frequency magnetic field using the average value of strengths of the output gradient magnetic field waveforms, and calculates the phase variation using a phase variation per cycle caused by the output gradient magnetic field waveform.

4. The magnetic resonance imaging apparatus according to claim 1, wherein the high-frequency magnetic field determining unit further comprises:
an input gradient magnetic field determining unit configured to determine the input gradient magnetic field waveform from imaging parameters; and
an output gradient magnetic field determining unit configured to determine the output gradient magnetic field waveform from the input gradient magnetic field waveform.

5. The magnetic resonance imaging apparatus according to claim 4, further comprising:
a storage device configured to store a pre-calculated output gradient magnetic field waveform by corresponding to the input gradient magnetic field waveform for each of the input gradient magnetic field waveforms and imaging parameters, wherein
the output gradient magnetic field determining unit determines the output gradient magnetic field waveform by extracting an output gradient magnetic field waveform corresponding to the input gradient magnetic field waveform from the storage device.

6. The magnetic resonance imaging apparatus according to claim 4, wherein the output gradient magnetic field determining unit determines the output gradient magnetic field waveform by comparing a first result obtained by executing a predetermined pulse sequence with application of a gradient magnetic field in an actual imaging and a second result obtained by executing the pulse sequence without application of the gradient magnetic field.

7. The magnetic resonance imaging apparatus according to claim 4, wherein:
the calculation unit is configured to calculate a correlation coefficient from plural output gradient magnetic field waveforms; and the output gradient magnetic field determining unit determines the output gradient magnetic field waveform using the imaging parameter and the correlation coefficient.

8. The magnetic resonance imaging apparatus according to claim 4, wherein the output gradient magnetic field determining unit determines the output gradient magnetic field waveform by performing convolution integral using the input gradient magnetic field waveform and a predetermined system transfer function.

9. The magnetic resonance imaging apparatus according to claim 4, wherein the output gradient magnetic field determining unit determines the output gradient magnetic field waveform using an oblique angle which is input by a user.

10. A magnetic resonance imaging apparatus comprising:
a magnet which generates a static magnetic field;
a gradient magnetic field generating unit configured to apply a gradient magnetic field in a static magnetic field space;
a high-frequency magnetic field applying unit configured to apply a high-frequency magnetic field to an object to be examined;
a signal detecting unit configured to detect a nuclear magnetic resonance signal generated from the object;
a measurement control unit configured to control operation of the gradient magnetic field generating unit, the high-frequency magnetic field applying unit and the signal detecting unit; and
a calculation unit configured to issue a command to the measurement control unit to control in accordance with a redetermined pulse sequence and perform calculation including reconstruction of an image from nuclear magnetic resonance signals detected by the signal detecting unit,
wherein the calculation unit comprises:
a high-frequency magnetic field determining unit configured to determine high-frequency magnetic field information to be applied from the high-frequency magnetic field applying unit on the basis of an output gradient magnetic field waveform which is applied by the gradient magnetic field generating unit in accordance with an input gradient magnetic field waveform which is input according to the pulse sequence; and
a sequence creating unit configured high-frequency magnetic field information determined by the high-frequency magnetic field determining unit in the pulse sequence,
wherein the calculation unit is configured to calculate irradiation frequency of the high-frequency magnetic field using the output gradient magnetic field waveform and is configured to calculate the phase variation caused by the change of an applied gradient magnetic field from the input gradient magnetic field waveform to the output gradient magnetic field waveform,
wherein the sequence creating unit sets the calculated phase variation in the high-frequency magnetic field information of the pulse sequence, and
wherein the sequence creating unit sets the calculated irradiation frequency in the high-frequency magnetic field information of the pulse sequence as a modulating frequency.

11. A magnetic resonance imaging apparatus comprising:
a magnet which generates a static magnetic field;
a gradient magnetic field generating unit configured to apply a gradient magnetic field in a static magnetic field space;
a high-frequency magnetic field applying unit configured to apply a high-frequency magnetic field to an object to be examined;
a signal detecting unit configured to detect a nuclear magnetic resonance signal generated from the object;
a measurement control unit configured to control operation of the gradient magnetic field generating unit, the high-frequency magnetic field applying unit and the signal detecting unit; and
a calculation unit configured to issue a command to the measurement control unit to control in accordance with a predetermined pulse sequence and perform calculation including reconstruction of an image from nuclear magnetic resonance signals detected by the signal detecting unit,
wherein the calculation unit comprises:
a high-frequency magnetic field determining unit configured to determine high-frequency magnetic field information to be applied from the high-frequency magnetic field applying unit on the basis of an output gradient magnetic field waveform which is applied by the gradient magnetic field generating unit in accordance with an input gradient magnetic field waveform which is input according to the pulse sequence; and
a sequence creating unit configured to set high-frequency magnetic field information determined by the high-frequency magnetic field determining unit in the pulse sequence,
wherein the calculation unit is configured to calculate the phase variation caused by the change of an applied gradient magnetic field from the input gradient magnetic field waveform to the output gradient magnetic field waveform,
wherein the sequence creating unit sets the calculated phase variation in the high-frequency magnetic field information of the pulse sequence, and
wherein:
the calculation unit is configured to calculate an amplitude waveform of the high-frequency magnetic field using the input gradient magnetic field waveform and the output gradient magnetic field waveform; and
the sequence creating unit sets the calculated amplitude waveform in the high-frequency magnetic field information of the pulse sequence.

12. A high-frequency method in a magnetic resonance imaging apparatus, which determines high-frequency magnetic field information to be set in a pulse sequence to be used for imaging, including high-frequency magnetic field calculation that calculates the high-frequency magnetic field information on the basis of an output gradient magnetic field waveform to be a lied in accordance with an input gradient magnetic field waveform which is set in the pulse sequence,
wherein the high-frequency magnetic field calculation comprises:
frequency calculation that calculates frequency of the high-frequency magnetic field using the average value of the output gradient magnetic field waveforms; and
phase calculation that calculates the phase variation of an applied high-frequency magnetic field waveform caused by the change of the input gradient magnetic field waveform to the output gradient magnetic field waveform.

* * * * *